US012116327B2

(12) United States Patent
Lindblad et al.

(10) Patent No.: US 12,116,327 B2
(45) Date of Patent: Oct. 15, 2024

(54) SELECTIVE HYDROXYL GROUP REMOVAL FROM ALKYLPHENOLS

(71) Applicant: Neste Oyj, Espoo (FI)

(72) Inventors: Marina Lindblad, Porvoo (FI); Kaisa Lamminpää, Porvoo (FI); José Luis González Escobedo, Porvoo (FI); Reetta Karinen, Aalto (FI); Eveliina Mäkelä, Porvoo (FI); Riikka Puurunen, Aalto (FI)

(73) Assignee: NESTE OYJ, Espoo (FI)

(*) Notice: Subject to any disclaimer, the term of this patent is extended or adjusted under 35 U.S.C. 154(b) by 351 days.

(21) Appl. No.: 17/415,379

(22) PCT Filed: Dec. 18, 2019

(86) PCT No.: PCT/FI2019/050904
§ 371 (c)(1),
(2) Date: Jun. 17, 2021

(87) PCT Pub. No.: WO2020/128161
PCT Pub. Date: Jun. 25, 2020

(65) Prior Publication Data
US 2022/0064079 A1    Mar. 3, 2022

(30) Foreign Application Priority Data
Dec. 21, 2018  (FI) .................... 20186130

(51) Int. Cl.
C07C 1/22      (2006.01)
B01J 19/00     (2006.01)
(Continued)

(52) U.S. Cl.
CPC ............. *C07C 1/22* (2013.01); *B01J 19/0013* (2013.01); *B01J 19/245* (2013.01);
(Continued)

(58) Field of Classification Search
CPC ........ C07C 1/22; B01J 19/0013; B01J 19/245
See application file for complete search history.

(56) References Cited

U.S. PATENT DOCUMENTS 9,758,731 B2      9/2017  Rinaldi et al.
2011/0237838 A1*  9/2011  Zmierczak ............... C10G 3/49
                                               568/749
(Continued)

FOREIGN PATENT DOCUMENTS

CN    104387223 A     3/2015
CN    104744204 A     7/2015
(Continued)

OTHER PUBLICATIONS

Machine Translation of CN 106753549 A (Year: 2017).*
(Continued)

Primary Examiner — Ellen M McAvoy
Assistant Examiner — Ming Cheung Po
(74) Attorney, Agent, or Firm — Buchanan Ingersoll & Rooney PC

(57) ABSTRACT

A process for selective removal of hydroxyl groups from phenolic compounds is disclosed. The process uses a combination of catalytic hydrodeoxygenation and catalytic direct deoxygenation to convert alkylphenols into alkylbenzenes.

19 Claims, 9 Drawing Sheets

Figure 1A:
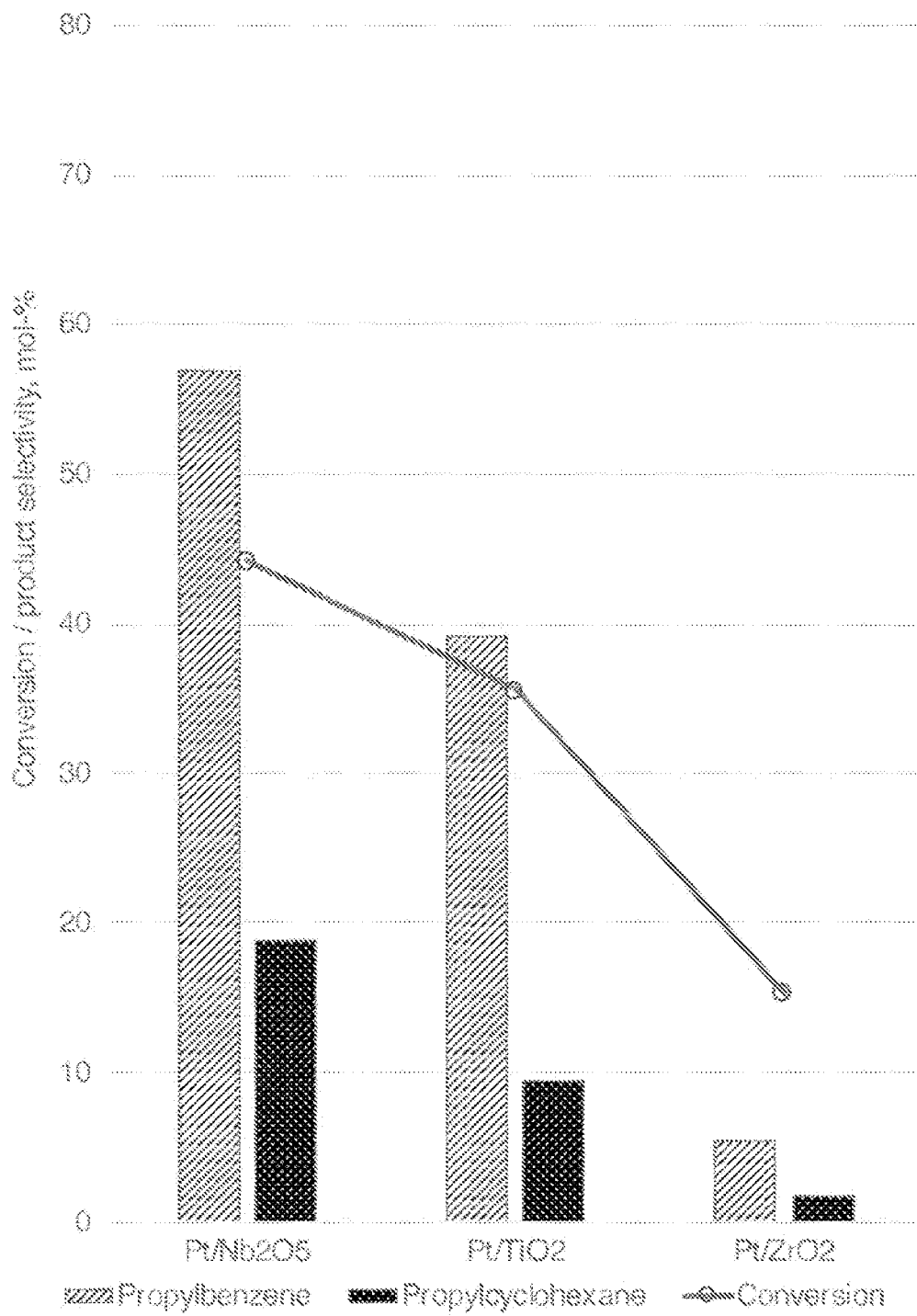

(51) Int. Cl.
  *B01J 19/24* (2006.01)
  *B01J 23/648* (2006.01)
  *B01J 23/882* (2006.01)
  *B01J 23/883* (2006.01)
  *B01J 23/888* (2006.01)

(52) U.S. Cl.
  CPC ......... *B01J 23/6484* (2013.01); *B01J 23/882* (2013.01); *B01J 23/883* (2013.01); *B01J 23/8885* (2013.01); *B01J 2219/0004* (2013.01); *B01J 2219/00051* (2013.01); *C07C 2523/648* (2013.01); *C07C 2523/882* (2013.01); *C07C 2523/883* (2013.01); *C07C 2523/888* (2013.01)

(56) References Cited

U.S. PATENT DOCUMENTS

| | | | |
|---|---|---|---|
| 2012/0222349 A1* | 9/2012 | Truitt | C10G 3/50 44/349 |
| 2014/0275666 A1 | 9/2014 | Bauer et al. | |
| 2016/0145172 A1 | 5/2016 | Baird et al. | |

FOREIGN PATENT DOCUMENTS

| | | | | |
|---|---|---|---|---|
| CN | 106495974 A | | 3/2017 | |
| CN | 106753549 A | * | 5/2017 | ......... B01J 23/6484 |
| CN | 107903144 A | | 4/2018 | |
| CN | 108993495 A | | 12/2018 | |
| EP | 2631224 B1 | | 9/2018 | |
| KR | 20130043000 A | | 4/2013 | |
| WO | 2013169112 A1 | | 11/2013 | |
| WO | 2017078582 A1 | | 5/2017 | |

OTHER PUBLICATIONS

Tianye Guo, Qineng Xia, Yi Shao, Xiaohui Liu, Yanqin Wang, Direct deoxygenation of lignin model compounds into aromatic hydrocarbons through hydrogen transfer reaction, Applied Catalysis A, General 547 (2017) 30-36 (Year: 2017).*
Ferrando et al., "Hydrogen/hydrocarbon phase equilibrium modelling with a cubic equation of state and a Monte Carlo method", Science Direct, 2007, pp. 211-223.
Reid et al., "The Properties of Gases & Liquids", Fourth Edition, Chemical Engineering, McGraw-Hill, Inc., 1987, pp. 1-753.
Hemptinne et al., Phase Equilibrium in Presence of H2 or Other Supercritical Gases. In Select Thermodynamic Models for Process Simulation—A Practical Guide Using a Three Steps Methodology; Editions Technip, 2012; p. 289.
Office Action (Communication) issued on Jun. 3, 2022, by the European Patent Office in corresponding European Patent Application No. 19 828 811.0. (7 pages).
Céondo GmbH. Chemical Properties of Phenol, 4-propyl-(CAS 645-56-7_=) https://www.chemeo.com/cid/27-374-7/Phenol%2C 4-propyl-#ref-joback (Online. Accessed Aug. 6, 2018, retrieved Jun. 14, 2021), 2 pages.
Dong et al., "Comparison of two multifunctional catalysts [M/Nb2O5 (M = Pd, Pt)] for one-pot hydrodeoxygenation of lignin", Catalysis Science & Technology, Royal Society of Chemistry, 2018, pp. 6129-6136.
Finnish Search Report issued in corresponding U.S. Appl. No. 20/186,130 dated Mar. 26, 2019.
Guo et al., "Direct deoxygenation of lignin model compounds into aromatic hydrocarbons through hydrogen transfer reaction", Applied Catalysis A, General, Accepted Apr. 11, 2017, pp. 30-36.
International Search Report (PCT/ISA/210) and Written Opinion (PCT/ISA/237) mailed on Jul. 13, 2020, by the Finnish Patent Office as the International Searching Authority for International Application No. PCT/FI2019/050904.
Notification of Transmittal of the International Preliminary Report of Patentability issued in International Application No. PCT/FI2019/050904 dated Mar. 29, 2021.
Finnish Office Actions three (3), issued in corresponding U.S. Appl. No. 20/186,130 dated Mar. 26, 2019, Mar. 27, 2020, and Aug. 6, 2020.
U.S. Secretary of Commerce on behalf of the United States of America. Phenol, 4-propyl- https://webbook.nist.gov/cgi/cbook.cgi?ID=C645567&Mask=4 (accessed Jul. 25, 2018, retrieved Jun. 4, 2021), 3 pages.
Y. Zhang et al., "Catalytic Hydroprocessing of Lignin", CIESC Journal, Mar. 2017, pp. 821-830, vol. 68, No. 3.
Y. Shao et al., "Selective Production of Arenes via Direct Lignin Upgrading Over a Niobium-based Catalyst", Nature Communications, Jul. 24, 2017, pp. 1-9.
First Office Action issued on Jul. 13, 2022, by the Chinese Patent Office in corresponding Chinese Patent Application No. 201980084734.3, and an English Translation of the Office Action. (15 pages).

* cited by examiner

SELECTIVE HYDROXYL GROUP REMOVAL FROM ALKYLPHENOLS

FIELD OF THE INVENTION

The present invention relates to the processing of hydroxyaromatic compounds, in particular to removing oxygen from phenolic oxygen-containing hydrocarbon feedstocks.

BACKGROUND

Biofuels and biomass-derived chemicals are used as sustainable alternatives for fossil products. For example lignocellulosic biomass can be used as a source of hydrocarbons. However, due to the high oxygen content lignocellulosic biomass derived liquids, such as bio oils and biocrudes, have low heating value, poor thermal stability, low volatility and corrosiveness.

When oxygen removal from lignocellulosic biomass derived liquids was studied it was observed that high degree of oxygen removal was only achieved at severe reactions conditions (high temperature and high $H_2$ pressure) due to the presence of highly refractory phenolic compounds. Alkylphenols were identified as the last type of oxygenates remaining in hydrotreated products with very low oxygen content.

Thus, it would be desirable to be able to convert alkylphenols selectively to alkylbenzene, to remove oxygen. For example it would be desirable to convert propylphenol to propylbenzene with little production of propylcyclohexane. Hydrodeoxygenation catalyst containing niobium oxide is disclosed for example in EP2631224B1 (SK INNOVATION, 2011), which discloses a method for producing hydrocarbons from biomass or organic waste. Catalyst includes a material selected from the group consisting of $CeZrO_x$, $CuZrO_x$, hydrotalcite, niobium oxide, alumina, silica, silica-alumina, zirconia, titania, oxide mixtures thereof, molecular sieves including zeolite, Pd, Pt, Rh, Ru, Ni, NiMo, CoMo, NiW, and CoW.

Hydrodeoxygenation of lignocellulosic feed (lignin oil) is disclosed for example in WO 2017/078582 (SCA) where hydrodeoxygenation catalyst is selected from Ni/NiO, Cu/Cr, Pd/Cu, or Pt on a support material, such as chromite and/or alumina and/or zirconia and/or graphite and/or carbon and/or silica.

HDO of phenols is described for example in U.S. Pat. No. 9,758,731 (STUDIENGESELLSCHAFT KOHLE MBH), which discloses a process for the selective hydrodeoxygenation of phenolic feeds into aromatic hydrocarbons by subjecting the phenolic feeds to a one-pot hydrotreatment in absence of external supply of molecular hydrogen. Catalyst metal is selected from nickel, iron, cobalt, copper, ruthenium, palladium, rhodium, osmium iridium, rhenium or mixtures thereof.

SUMMARY

The inventors have found that it is possible to use a specific metal catalyst system to selectively remove oxygen from hydroxyaromatic hydrocarbon compounds while preserving a significant portion of their aromaticity. Because saturating aromatic rings requires hydrogen, and because aromaticity is preserved in the present process, the present process reduces significantly the consumption of hydrogen and improves the total GHG (greenhouse gas) savings e.g. when producing hydrocarbons from lignocellulosic biomass derived feedstocks. In gasoline and jet fuel applications it is beneficial to at least partly preserve the aromaticity of the fuel.

According to the first aspect is provided a process for removing hydroxyl groups from phenolic compounds, comprising:
Providing in a first reactor at least one hydrodeoxygenation catalyst comprising sulphided NiMo, CoMo or NiW;
Providing a feedstock comprising phenolic compounds;
Carrying out hydrodeoxygenation by contacting the feedstock with the hydrodeoxygenation catalyst to obtain a phenolic hydrocarbon feedstock;
Providing in a second reactor at least one direct deoxygenation catalyst comprising $Pt/Nb_2O_5$;
Forming a mixture by feeding into the second reactor the phenolic hydrocarbon feedstock and hydrogen gas;
Carrying out direct deoxygenation to the phenolic hydrocarbon feedstock to obtain hydrocarbons, wherein at least 50 mol-% of the hydroxyl groups originally bonded to phenolic compounds are removed while the aromaticity of the hydrocarbon is preserved.

An advantage of the present process is high selectivity and low consumption of hydrogen. Further, selectivity and yield of the catalytic conversion of phenolics can be controlled in the present invention by adjusting the process parameters, because the catalysts allow a certain degree of freedom in the reaction conditions. Advantageously, with the present process side reactions such as dealkylation, benzene formation, oligomerization, or condensation to compounds outside fuel range, are avoided.

According to the second aspect is provided a use of $Pt/Nb_2O_5$ catalyst in selective conversion of hydroxyaromatic compounds in hydrocarbon feedstock to aromatic compounds. In an embodiment said aromatic compounds do not contain oxygen.

For example alkylphenols can be converted into alkylbenzenes by the present method.

An advantage of the invention is that only hydroxyl in phenolic compounds of the hydrocarbon feedstock is removed and only the phenolic compounds are converted to corresponding aromatic hydrocarbons.

According to the third aspect is provided a catalytic conversion system comprising a first reactor and a second reactor wherein:
The first reactor is in fluid communication with the second reactor;
The first reactor comprises:
At least one hydrodeoxygenation catalyst bed comprising sulphided NiMo, CoMo, NiW or a combination thereof;
Temperature control means for monitoring and adjusting temperature inside the first reactor;
At least one first inlet for feeding phenolic compounds into the first reactor;
At least one second inlet for feeding hydrogen into the first reactor;
At least one first outlet for transferring the resulting phenolic hydrocarbon feedstock outside the first reactor; and
The second reactor comprises:
at least one direct deoxygenation catalyst bed comprising $Pt/Nb_2O_5$;
temperature control means for monitoring and adjusting temperature inside the second reactor
At least one third inlet for feeding phenolic hydrocarbons into the second reactor;

At least one fourth inlet for feeding hydrogen into the second reactor;

At least one second outlet for transferring the resulting feedstock comprising aromatic compounds outside the second reactor; and Wherein the second reactor optionally comprises at least one recycle feed line from the second outlet to the third inlet.

An advantage of the present catalytic conversion system is synergistic deoxygenation of the feedstock. Because the deoxygenation is carried out in two steps and with different reaction routes, it is possible to effectively remove oxygen from the hydrocarbons of the feedstock while simultaneously keeping the aromatic compounds unsaturated. This results into a system with which it is possible to achieve a high deoxygenation rate with a low hydrogen consumption. Further alkylphenols are not saturated during the process. Preferably the process of the first aspect is carried out in the catalytic conversion system of the third aspect.

In an embodiment the process of the first aspect is carried out in the catalytic conversion system of the third aspect.

FIGURES

Figure 1B:
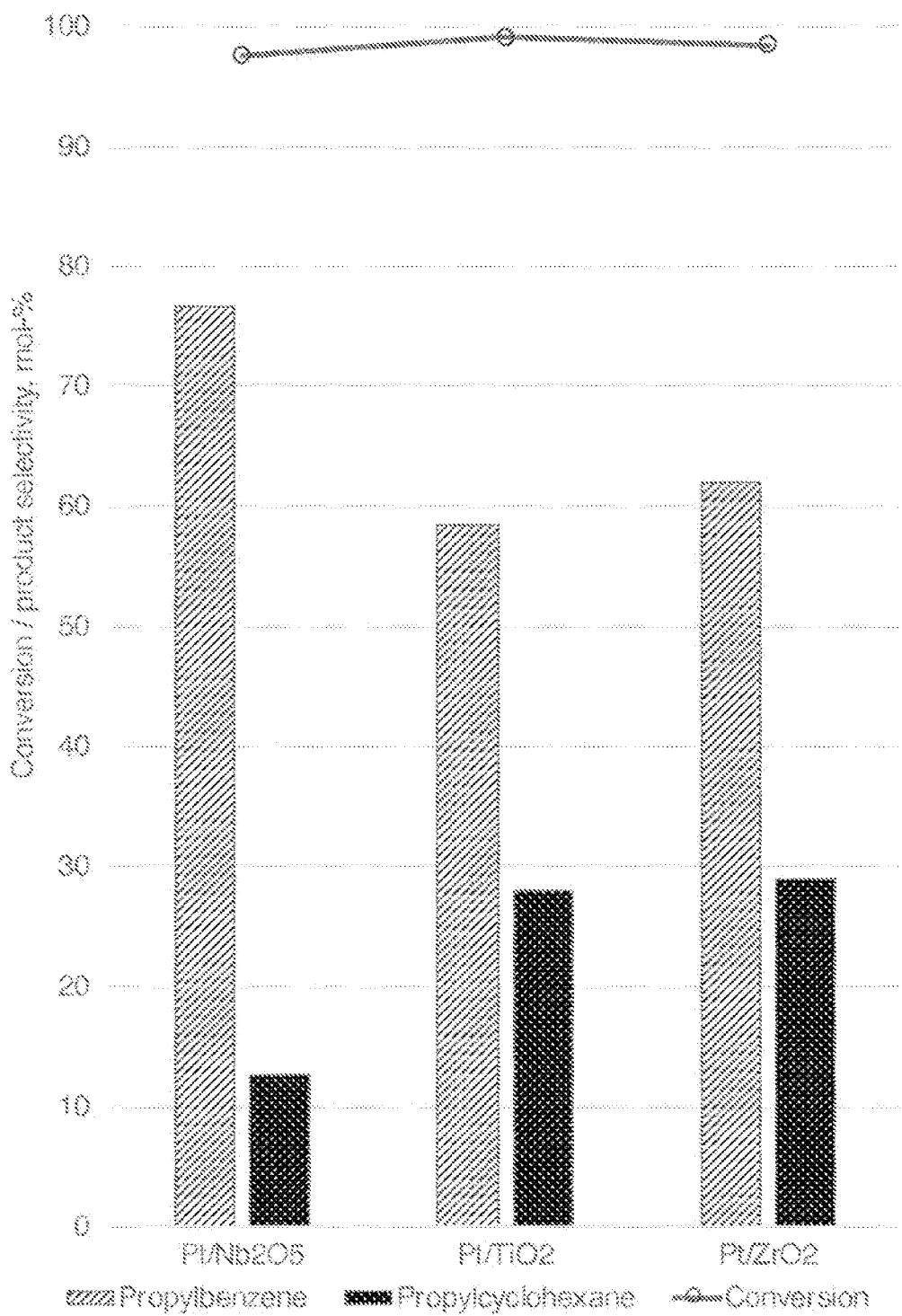

FIG. 1. Comparison of platinum catalysts with different supports (niobia, titania and zirconia) for HDO of 4-propylphenol. The three catalysts were reduced at 20 bar $H_2$ and 353° C. for 60 min. FIG. 1A) Comparison at low residence time. Conditions: 20 bar, 350° C., T=0.25 $min \cdot mg_{catalyst} \cdot mg_{reactant}^{-1}$. FIG. 1B) Comparison at full conversion. Conditions: 20 bar, 350° C., T=4 min $mg_{catalyst} \cdot mg_{reactant}^{-1}$.

Figure 2:
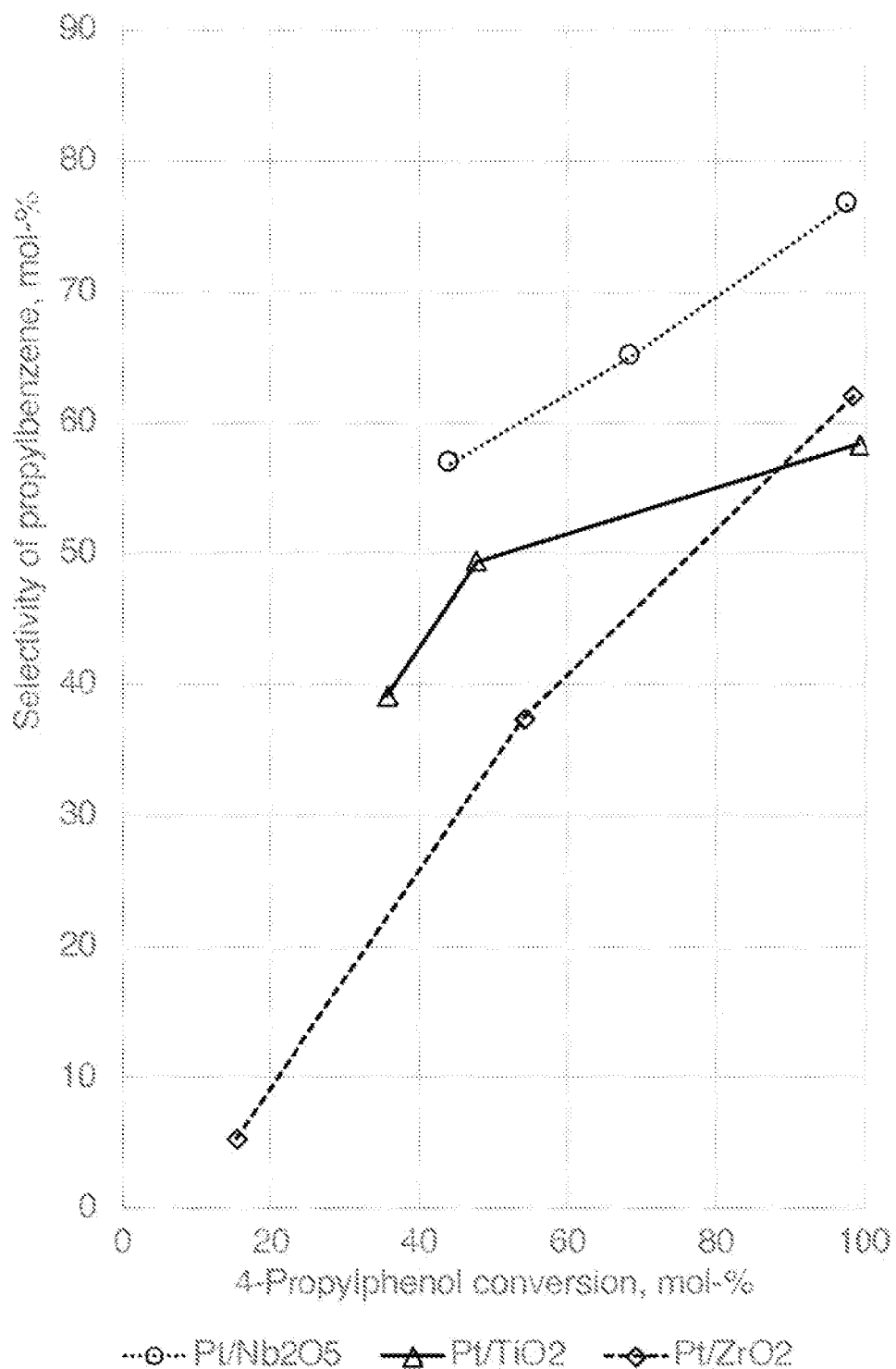

FIG. 2. Selectivity for propylbenzene formation in HDO of 4-propylphenol with three platinum catalysts supported on different oxide materials (niobia, titania, zirconia). Conditions: 20 bar, 353° C., T=0.2-4.1 $min \cdot mg_{catalyst} \cdot mg_{reactant}^{-1}$.

Figure 3:
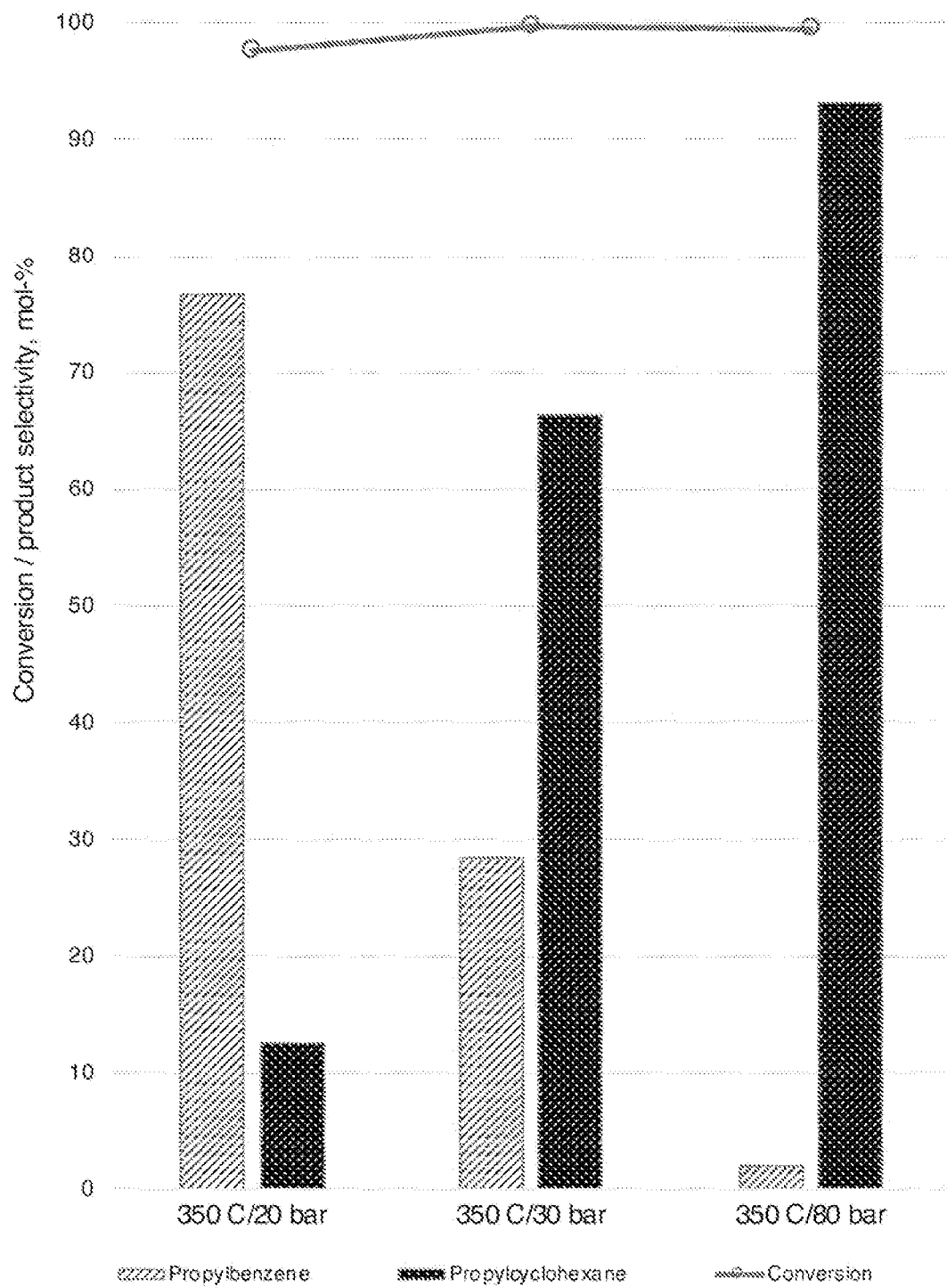

FIG. 3. Selectivities for propylbenzene and propylcyclohexane formation in HDO of 4-propylphenol at various reaction pressures (350° C., residence time of 4 $min \cdot mg_{catalyst} \cdot mg_{reactant}^{-1}$).

Figure 4A:
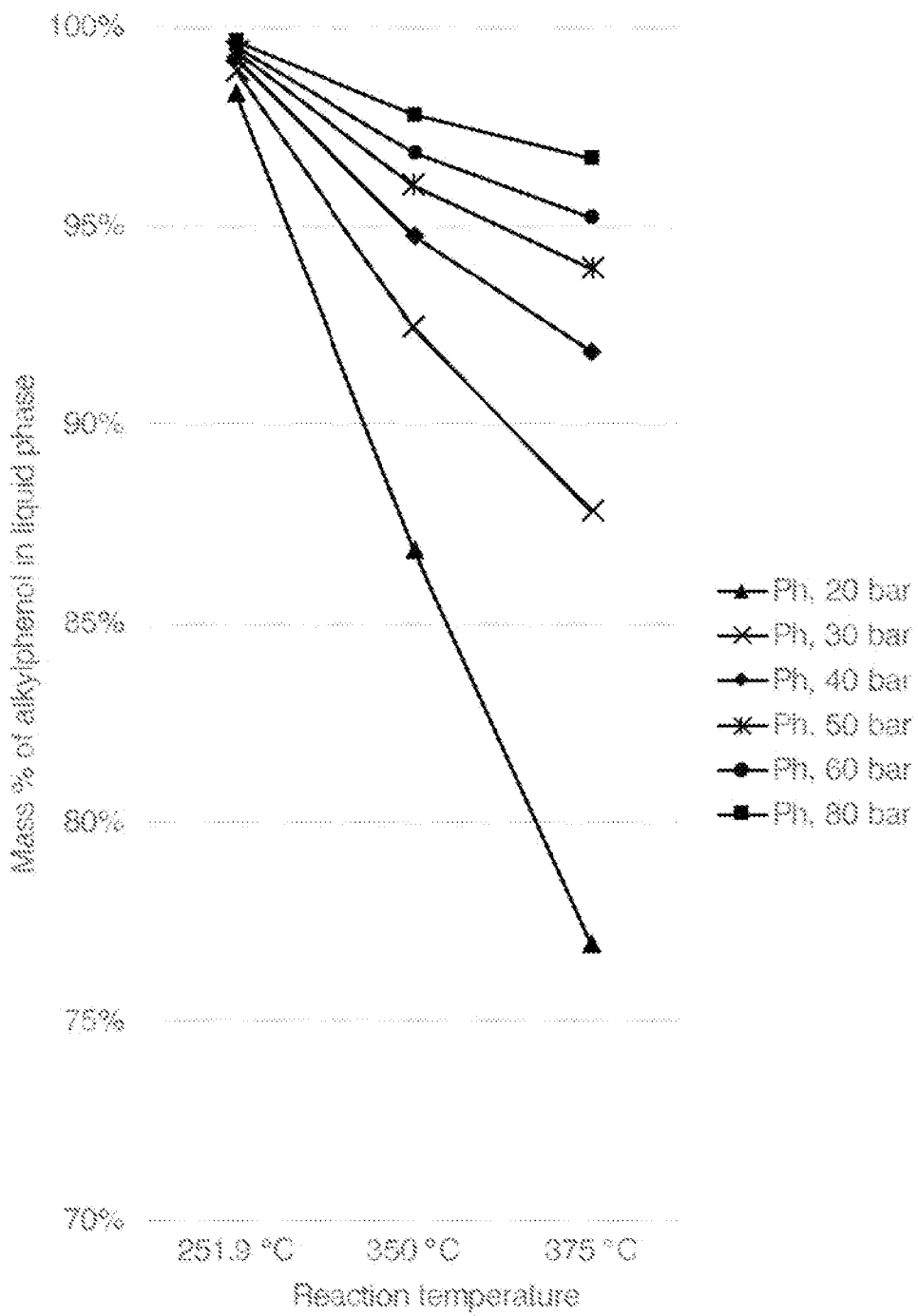
Figure 4B:
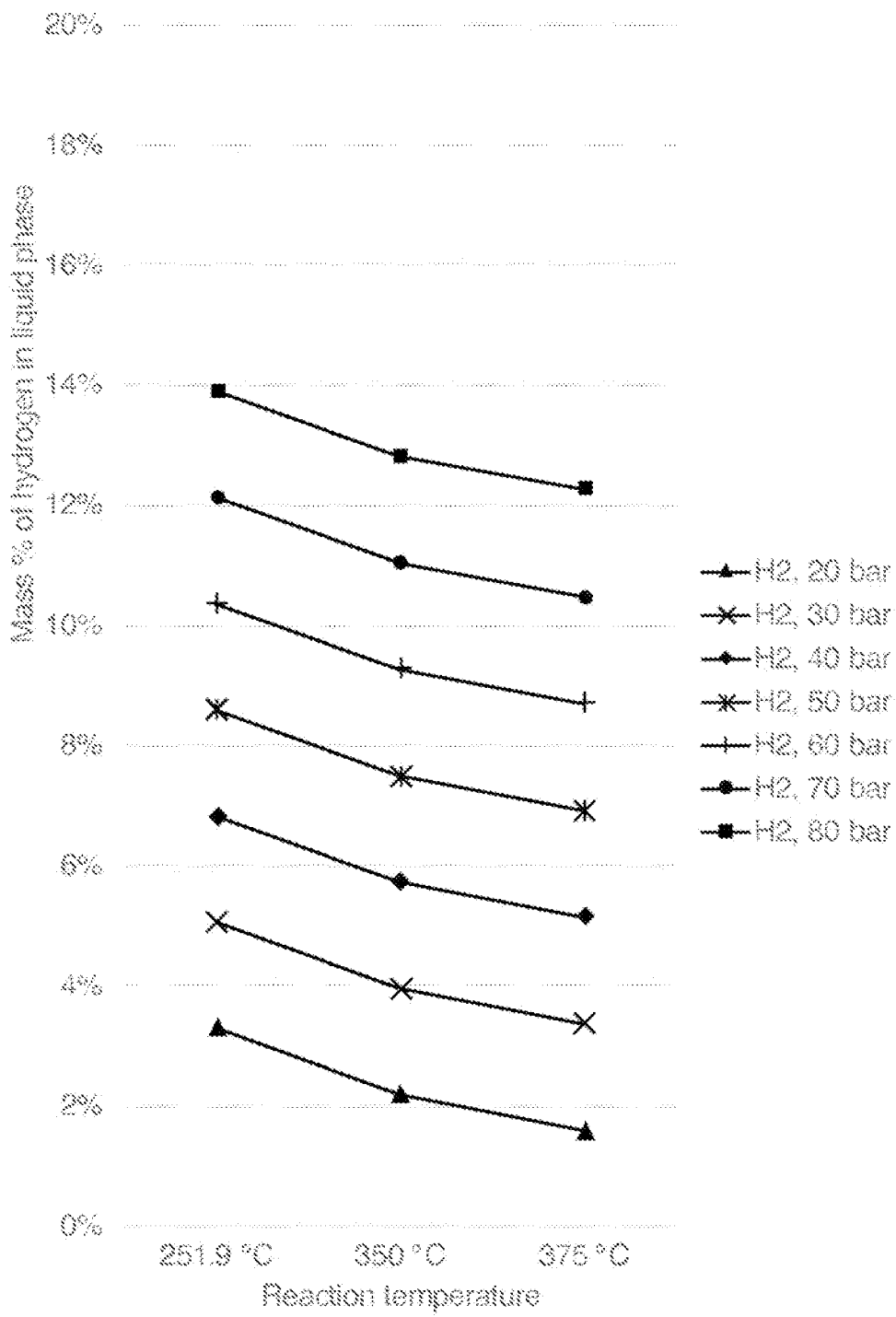

FIG. 4. UNIQUAC calculations (Aspen) of VLE of the initial amounts of reactants in a typical experiment. Amounts: 56 mg $H_2$, 580 mg alkylphenol, 27 mL tetradecane (solvent). FIG. 4A) temperature dependence of percentage of mass of alkylphenol in the liquid phase at 20-80 bar. FIG. 4B) Temperature dependence of percentage of mass of $H_2$.

Figure 5:
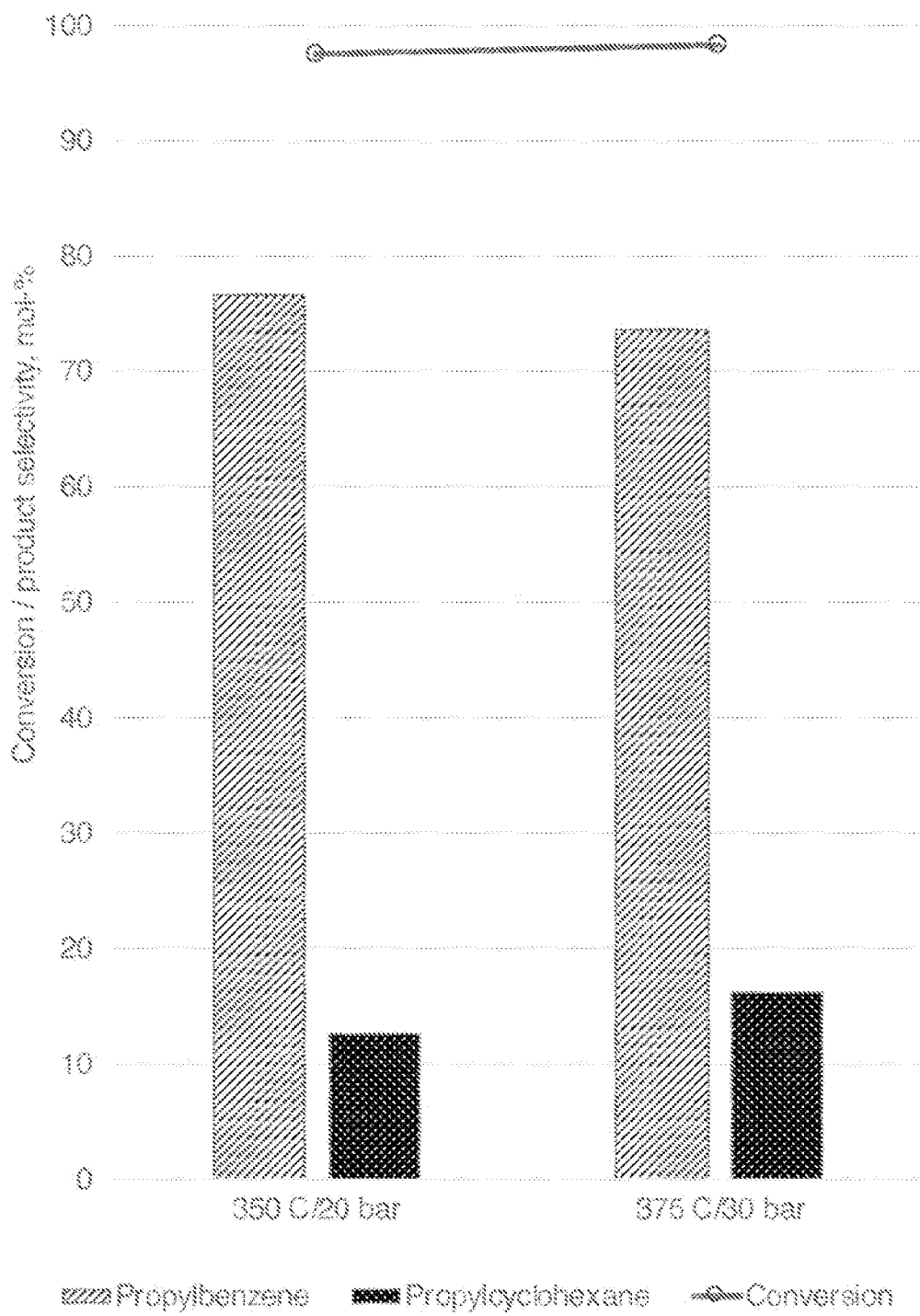

FIG. 5. Selectivities for propylbenzene and propylcyclohexane formation in HDO of 4-propylphenol at 350° C./20 bar and 375° C./30 bar (residence time of 4 $min \cdot mg_{catalyst} \cdot mg_{reactant}^{-1}$).

Figure 6:
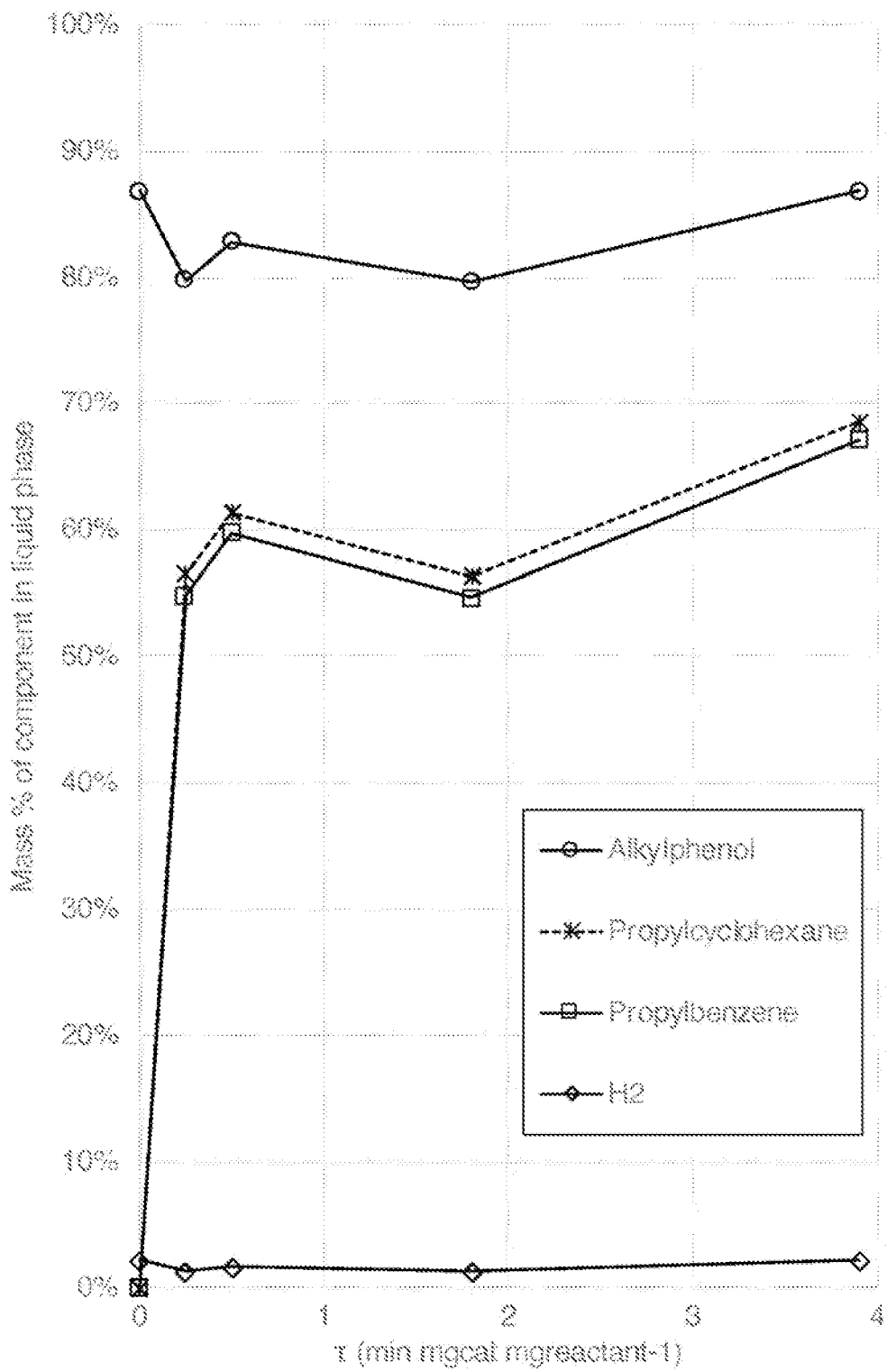

FIG. 6. UNIQUAC calculations (Aspen) of VLE at the end (before cooling in the autoclave experiment) of selected experiments at various residence times. Conditions: 20 bar, 350° C., 100 mL batch. Percentage of mass of components in the liquid phase.

Figure 7:
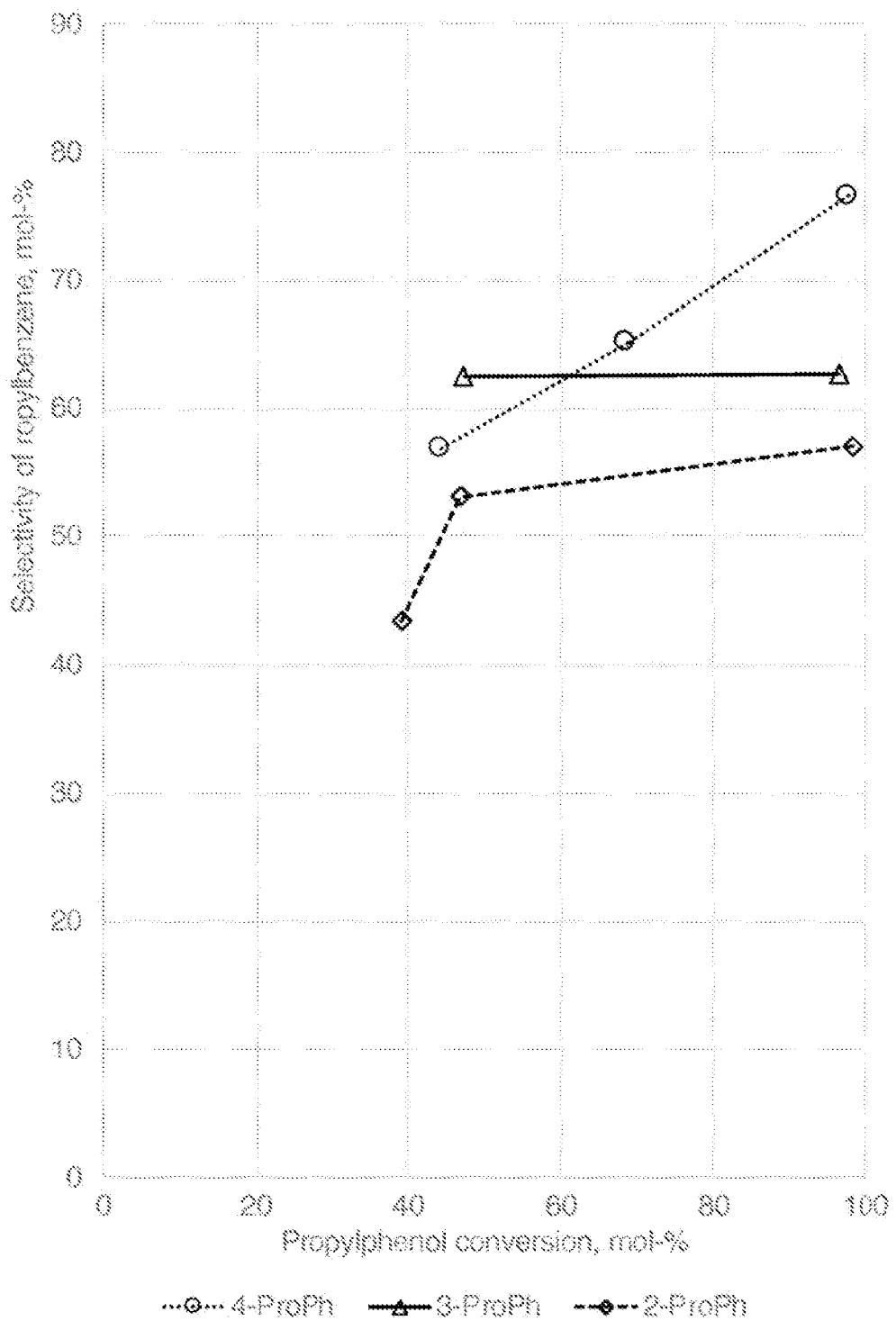

FIG. 7. Selectivity for propylbenzene formation in HDO of para-, meta- and ortho isomers of propylphenol over Pt/Nb$_2$O$_5$ catalyst (350° C., 20 bar and various residence times).

DETAILED DESCRIPTION OF THE INVENTION

As used herein, the term "comprising" includes the broader meanings of "including", "containing", and "comprehending", as well as the narrower expressions "consisting of" and "consisting only of".

In an embodiment the process is carried out in an industrial scale.

In an embodiment the steps of the present process are carried out in the sequence specified in the embodiment. In another embodiment any process step specified to be carried out to a product or intermediate obtained in a preceding process step, is carried out directly to said product or intermediate, i.e. without additional or auxiliary processing steps that may chemically or physically alter the product or intermediate between said two consecutive steps.

Biocrudes and bio oils are produced from biomass, in particular from lignocellulosic biomass, with various liquefying methods, such as hydrothermal liquefaction, or pyrolysis, in particular fast pyrolysis.

The term "biocrude" refers to oils produced from biomass by employing hydrothermal liquefaction.

The term "bio oil" refers to pyrolysis oils produced from biomass by employing pyrolysis.

The term "biomass" refers to material derived from recently living organisms, which includes plants, animals and their byproducts.

The term "lignocellulosic biomass" refers to biomass derived from plants or their byproducts. Lignocellulosic biomass is composed of carbohydrate polymers (cellulose, hemicellulose) and an aromatic polymer (lignin).

The term "pyrolysis" refers to thermal decomposition of materials at elevated temperatures in a non-oxidative atmosphere.

The term "fast pyrolysis" refers to thermochemical decomposition of biomass through rapid heating in absence of oxygen.

The term "hydrothermal liquefaction" (HTL) refers to a thermal depolymerization process used to convert wet biomass into crude-like oil under moderate temperature and high pressure.

Examples of bio oil and biocrude produced from lignocellulosic biomass, e.g. materials like forest harvesting residues or byproducts of a saw mill, are lignocellulosic pyrolysis liquid (LPL), produced by employing fast pyrolysis, and HTL-biocrude, produced by employing hydrothermal liquefaction.

Further examples of lignocellulosic biomass derived liquids include crude tall oil (CTO), obtained as a by-product of the Kraft process (wood pulping), and its derivatives, such as tall oil pitch (TOP), crude fatty acid (CFA), tall oil fatty acid (TOFA) and distilled tall oil (DTO).

The term HDO refers to at least partial hydrodeoxygenation of hydroxyl and other oxygen-containing groups.

In an embodiment hydrogen gas is fed into the first reactor during hydrodeoxygenation.

The term HYD refers to HDO by hydrogenation-dehydration-hydrogenation route.

In the present process hydrodeoxygenation is a HDO process.

The term DDO refers to at least partial direct deoxygenation, which directly cleaves the C—O bond by hydrogenolysis, and which does not require intermediate hydrogenation steps. In the present process the catalytic conversion with Pt/Nb$_2$O$_5$ is a DDO process.

The term WHSV refers to weight of feed flowing per weight of the catalyst per hour.

In an embodiment the reactor is operated in a continuous mode.

In an embodiment the reactor is a fixed bed reactor.

A phenolic compound is a compound comprising at least one hydroxyl group bonded directly to an aromatic ring of an aromatic hydrocarbon. In the present invention the feedstock fed into the first reactor may contain phenolic compounds. The phenolic hydrocarbon feedstock fed into the second reactor also contains phenolic compounds. In an embodiment phenolic compounds are formed during the hydrodeoxygenation.

In an embodiment the phenolic hydrocarbon feedstock comprises recycled feed obtained after the DDO process. This embodiment is advantageous when the process is carried out in conditions where the catalytic deoxygenation is not complete, but a higher deoxygenation of the phenolic compounds is desired. Thus, in this embodiment the recycled feed contains phenolic compounds that can be deoxygenated with the present process by feeding them into the second reactor. The recycled feed can also be fed to the second reactor together with a fresh feed of the phenolic hydrocarbon feedstock from the first reactor.

In an embodiment the recycled feed from the second reactor, or the phenolic hydrocarbon feed obtained from renewable organic material from the first reactor, and to be treated by the present DDO process, contains high amount hydroxyl containing compounds. Examples of such hydroxyl containing compounds include plant based hydroxyaromatic hydrocarbon compounds and phenolic lipids such as cardanol. Further examples of hydroxyl containing compounds include animal fat based hydroxyl containing compounds such as sterols.

In an embodiment the phenolic hydrocarbon feedstock used in the second reactor is a feed obtained from hydrodeoxygenation. It is thus possible that the phenolic hydrocarbon feedstock fed into the second reactor from the first reactor is mixed with another feed which contains hydrodeoxygenated material.

The present process is carried out in two reactors: in a first reactor where hydrodeoxygenation is done, and in a second reactor where direct deoxygenation is done. In an embodiment the second reactor is in fluid connection with the first reactor. In another embodiment the phenolic hydrocarbon feedstock is a feedstock obtained after hydrodeoxygenating renewable hydrocarbon feed derived from plants or animals.

In an embodiment the phenolic hydrocarbon feedstock comprises alkylphenols, such as 4-propylbenzene. In another embodiment the alkylphenols comprise at least one of methylbenzene, dimethylbenzene, ethylbenzene.

In an embodiment the direct deoxygenation step is carried out at a temperature in the range 340-450° C., at a hydrogen pressure in the range 15-50 bar, preferably at 350° C. and 20 bar.

In an embodiment the phenolic hydrocarbon feedstock comprises alkylphenols.

In an embodiment the alkylphenols are converted to alkylbenzenes during the process.

In an embodiment the phenolic hydrocarbon feedstock is contacted with the catalyst in liquid phase. The skilled person is capable of calculating an appropriate temperature and pressure to be used in the reactor to keep the phenolic hydrocarbon feedstock, or at least the phenolic compounds in it, in liquid phase.

In an embodiment the phenolic hydrocarbon feedstock is reacted with the direct deoxygenation catalyst at a temperature in the range 340-450° C., more preferably in the range 340-400° C., 340-380° C., and even more preferably at about 350° C.

The temperature can be controlled by means known in the art, such as by heating and cooling the feed, the reactor, or both.

In embodiment the phenolic hydrocarbon feedstock is contacted with the catalyst in liquid phase.

In an embodiment the hydrodeoxygenation step is carried out at a temperature from 270 to 380° C., preferably from 275 to 360° C., more preferably from 300 to 350° C., at a hydrogen pressure from 30 to 100 bar, preferably from 40 to 80 bar and WHSV from 2 to 0.5 1/h. Preferably a temperature in the range 270-380° C., a hydrogen pressure in the range 30-100 bar and WHSV of 2-0.5 1/h is used. More preferably a temperature of 300-350° C., a pressure of 40-80 bar and WHSV from 2 to 0.5 1/h is used. These conditions are advantageous because they do not saturate aromatic rings of phenolic compounds.

Weight hourly space velocity (WHSV) is defined as the weight of feed flowing per hour divided by the weight of the catalyst.

In an embodiment the phenolic hydrocarbon feedstock is reacted with the direct deoxygenation catalyst at a pressure of about 15-50 bar, preferably at about 15-40 bar, about 15-30 bar and more preferably at about 20 bar.

In an embodiment the phenolic hydrocarbon feedstock is reacted with the direct deoxygenation catalyst at about 20 bar and about 350° C., or at about 30 bar and about 375° C.

In an embodiment pressure is controlled by feeding hydrogen into the first reactor and/or the second reactor.

In an embodiment the pressure and the temperature are selected during DDO such that at least 80%, preferably at least 90% of the alkylphenols remain in liquid phase during the process. For example at 20 bar and 350° C., 87% of alkylphenols are in liquid phase. At 30 bar and 375° C., 88% of alkylphenols are in liquid phase.

In another embodiment the pressure and the temperature are selected such that the hydrodeoxygenated reaction products evaporate at a greater extent to the gaseous phase than the reactants. Without being bound to a theory, this appears to have an advantage of avoiding contact with the aromatic reaction product and the catalyst, which helps to prevent saturation of the aromatic ring.

In an embodiment Pt is provided in the direct deoxygenation catalyst in metallic and optionally in an oxidized form. In an embodiment the Pt is provided in the catalyst in at least two different oxidized species. In an embodiment Pt present in the catalyst is partially in metallic state.

In an embodiment at least part of the feedstock comprising phenolic compounds is obtained from lignocellulosic biomass.

In an embodiment at least 50%, preferably at least 55%, 60%, 65%, 70% or 75% of the phenolic compounds of the phenolic hydrocarbon feedstock are converted to aromatic compounds. In an embodiment the amount of the phenolic compounds is measured by analyzing the end product.

In an embodiment no water or hydrogen sulfide is added in the reactor during the method. In another embodiment water and hydrogen sulfide are removed from the phenolic hydrocarbon feedstock before entering the process.

In another embodiment water is removed after hydrodeoxygenation. In an embodiment water removal is carried out in a water-removal unit.

The DDO of propylphenols was used in the examples to model the processing of some of the most HDO resistant oxygen-containing components in bio-oils, namely alkylphenols. In one embodiment of the reaction 4-propylphenol in tetradecane solvent in presence of a 3% $Pt/Nb_2O_5$ catalyst and at 350° C. and 20 bar $H_2$, provided a selectivity of ~70% towards the desired propylbenzene at full conversion. In this case, the thermodynamic features of the reaction system, such as the chemical equilibrium and the moderate $H_2$ solubility in to the solvent at the selected conditions, were selected for the desired selectivity and yield.

The highly successful results obtained with the para-isomer were similar but slightly attenuated for the corresponding ortho-isomer. Thus, the feedstock can contain both para-, meta- and ortho-isomers.

sumed in the removal of the phenolic group as water. An aromatic end product can also be formed after the HYD route if the aromaticity is restored in a dehydrogenation reaction after the removal of the phenolic group (HYD+ DeHYD).

A simplified depiction of the main routes for oxygen removal from propylphenol, the model compound used in the experiments, is shown in the reaction Scheme 1.

Scheme 1
Propylbenzene formation in HDO of propylphenol by the DDO route or by the HYD route followed by dehydrogenation of the ring structure

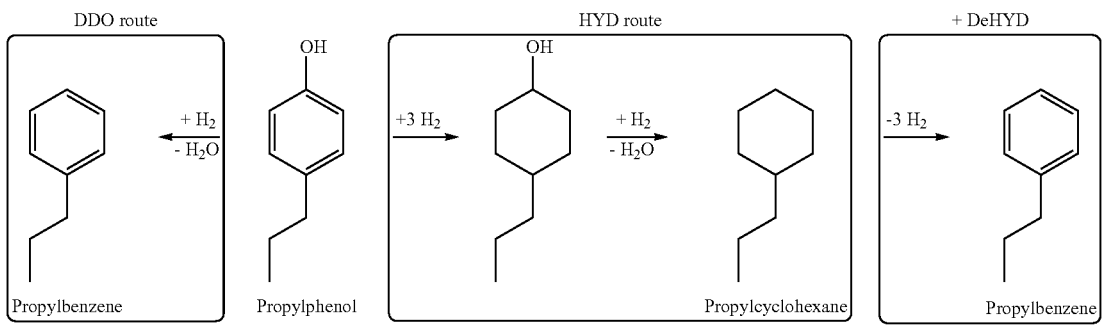

By comparing the performance of Pt catalysts supported on $Nb_2O_5$, $TiO_2$, and $ZrO_2$, it appeared that the catalysts with the reducible support ($Nb_2O_5$ i.e. niobia, $TiO_2$ i.e. titania) had a much higher activity compared to the non-reducible zirconia support. Furthermore, among the catalysts with the reducible supports, the niobia catalyst was more active and provided a higher selectivity to propylbenzene than the titania catalyst.

In the examples mainly 4-propylphenol was used as model compound of alkylphenols. The results obtained for this model compound can be generalised to feedstocks containing phenolic compounds, because alkylphenols are among the most difficult components e.g. in fast pyrolysis bio-oils to upgrade with HDO, due to the strength of the hydroxyl-arene bond. Thus, the challenges presented by alkylphenols, such as 4-propylphenol, represented well the challenges of different feedstocks.

The results of the DDO of propylphenols are presented and discussed below in the Examples. The outcome was that by tuning the reaction conditions, the thermodynamic equilibrium could be used to achieve a high selectivity towards the desired aromatic product. Lowering the pressure allowed the desired equilibrium to occur at lower temperatures, although a lower limit on the pressure was introduced by the requirement to operate in the liquid phase. Of the tested catalysts, $Pt/Nb_2O_5$ displayed a superior activity and was preferred. Catalysts with reducible metal oxides supports ($Nb_2O_5$, $TiO_2$) outperformed a catalysts with a non-reducible oxide support ($ZrO_2$).

The preferred reaction route for the removal of phenolic groups by HDO is commonly proposed to be the hydrogenation (HYD) route where the aromatic ring is hydrogenated prior to the removal of the phenolic group as water. The hydrogenation of the aromatic ring to cyclohexane consumes three times more hydrogen compared to the removal of the phenolic group. When using fossil based hydrogen, this will noticeable reduce the GHG savings needed for biofuel approval. Another route for oxygen removal from phenolic compounds is direct deoxygenation (DDO) were the aromatic ring is preserved and hydrogen is only con- The following clauses are provided to disclose embodiments of the invention.

Clauses

1. A process for removing hydroxyl groups from phenolic compounds, comprising: Providing in a first reactor at least one hydrodeoxygenation catalyst comprising sulphided NiMo, CoMo or NiW;
   Providing a feedstock comprising phenolic compounds;
   Carrying out hydrodeoxygenation by contacting the feedstock with the hydrodeoxygenation catalyst to obtain a phenolic hydrocarbon feedstock; Providing in a second reactor at least one direct deoxygenation catalyst comprising $Pt/Nb_2O_5$;
   Forming a mixture by feeding into the second reactor the phenolic hydrocarbon feedstock and hydrogen gas;
   Carrying out direct deoxygenation to the phenolic hydrocarbon feedstock to obtain hydrocarbons, wherein at least 50 mol-% of the hydroxyl groups originally bonded to phenolic compounds are removed while the aromaticity of the hydrocarbon is preserved.
2. The process of clause 1, wherein the hydrodeoxygenation is carried out at a temperature in the range 270-380° C., at a hydrogen pressure in the range 30-100 bar and WHSV of 2-0.5 1/h.
3. The process of clause 1 or 2, wherein the direct deoxygenation is carried out at a temperature in the range 340-450° C., at a hydrogen pressure in the range 15-50 bar, preferably at 350° C. and 20 bar.
4. The process of clauses 1-3, wherein the phenolic hydrocarbon feedstock comprises alkylphenols.
5. The process of clause 4, wherein alkylphenols are converted to alkylbenzenes during direct deoxygenation.
6. The process of clauses 1-5, wherein the phenolic hydrocarbon feedstock is contacted with the catalyst in liquid phase.

7. The process of clauses 1-6, wherein the feedstock is obtained from lignocellulosic biomass.
8. The process of clauses 1-7, wherein no water or hydrogen sulfide is added in the reactor during the method.
9. A catalytic conversion system comprising a first reactor and a second reactor wherein:
   The first reactor is in fluid communication with the second reactor;
   The first reactor comprises:
      At least one catalyst bed comprising sulphided NiMo, CoMo, NiW or a combination thereof;
      Temperature control means for monitoring and adjusting temperature inside the first reactor;
      At least one first inlet for feeding phenolic compounds into the first reactor;
      At least one second inlet for feeding hydrogen into the first reactor;
      At least one first outlet for transferring the resulting phenolic hydrocarbon feedstock outside the first reactor; and
   The second reactor comprises:
      at least one direct deoxygenation catalyst bed comprising Pt/$Nb_2O_5$;
      temperature control means for monitoring and adjusting temperature inside the second reactor
      At least one third inlet for feeding phenolic hydrocarbons into the second reactor;
      At least one fourth inlet for feeding hydrogen into the second reactor;
      At least one second outlet for transferring the resulting feedstock comprising aromatic compounds outside the second reactor; and
      Wherein the second reactor optionally comprises at least one recycle feed line from the second outlet to the third inlet.

EXAMPLES

The following examples are provided to illustrate various aspects of the present invention. They are not intended to limit the invention, which is defined by the accompanying claims.

Examples of the Selectivity for Propylbenzene Production Influence of Support Material for Platinum Catalyst The performance of three platinum catalysts at equal conditions was compared in order to examine the influence of the catalyst support on the HDO of 4-propylphenol. The catalysts were 3% Pt/$Nb_2O_5$, 3% Pt/$TiO_2$, and 3% Pt/$ZrO_2$. Before the HDO reactions, the catalysts were reduced at the same conditions. The results are presented in FIGS. 1A and 1B.

The difference between the three catalysts was clear both at low residence time and at full conversion of 4-propylphenol. At low residence time, the values of conversion and the selectivity to propylbenzene provided by the niobia catalyst exceeded the values obtained with the titania catalyst, which in turn outperformed the zirconia catalyst considerably. At full conversion, it was also observed that the niobia catalyst was able to suppress the formation of propylcyclohexane to a much greater extent compared to the other two catalysts.

The higher selectivity of Pt/$Nb_2O_5$—compared to Pt/$TiO_2$ and Pt/$ZrO_2$—for the formation of propylbenzene at various conversion levels of 4-propylphenol is shown in FIG. 2.

Influence of Reaction Pressure

The impact of reaction pressure was evaluated by conducting the HDO of 4-propylphenol at 20, 30, and 80 bar with temperature at 350° C. and all other conditions being equal. The reactions were allowed to attain full conversion. The results are shown in FIG. 3. Note that only pure $H_2$ was used to pressurize the reactor, hence a higher pressure implies a higher amount of $H_2$.

At full conversion, the yield to propylbenzene fell with respect to pressure, whilst the yield to propylcyclohexane increased. The fully hydrogenated product was favoured with more hydrogen available.

Influence of Reaction Temperature

The experimental study of the effects of reaction temperature required that the VLE were taken into account. Because of the small amount of reactant used, the possibility of evaporation at higher temperatures was a serious concern. For this reason, a series of VLE calculations were performed for the targeted temperatures and at different pressure. As input values the amounts of $H_2$, alkylphenol, and solvent that were typically fed to the reactor at the beginning of an experiment were used.

Influence of Position of Propylsubstituent

The selectivity for propylbenzene was compared for HDO of propylphenol with the propyl group substituted at para- (4-propylphenol), meta-(3-propylphenol) and ortho-(2-propylphenol) positions relative to the hydroxyl group (FIG. 7).

The selectivity for the formation of propylbenzene was similar at intermediate conversion of the para-, meta- and ortho-isomers of propylphenol. At nearly full conversion, the meta- and ortho-isomers did not achieve as high selectivity for propylbenzene as the para isomer.

The differences in conversion and product selectivities obtained with the three propylphenol isomers do not appear to be caused by thermodynamic limitations, as no differences among isomers were obtained in thermodynamic calculations. UNIQUAC calculations (by Aspens) of vapour-liquid-equilibrium (VLE) were carried out to estimate the temperature dependence of percentage of mass of $H_2$ and alkylphenol in the liquid phase at 20-80 bar (FIG. 4). Note that the mass percentage of component in the liquid phase represents the distribution of a given component among the phases, not the compositions of the liquid phase.

According to these calculations about 87% of the alkylphenol should be in the liquid phase in equilibrium at the initial state at 20 bar and 350° C. On the other hand, if the temperature increases from 350° C. to 375° C., while keeping the pressure at 20 bar, the percentage of alkylphenol in the liquid phase should drop to 77%. Hence, it appeared that the possibility of evaporating the reactant was significant. However, in the combination of 30 bar with 375° C., about 88% of the alkylphenol should be in the liquid phase. This distribution of alkylphenol among the phases is comparable to the distribution that can be expected at 20 bar and 350° C. Therefore, it was considered appropriate to use a pressure of 30 bar to test a temperature of 375° C. (see FIG. 5).

For the two reaction temperature-pressure-pairs selected based on the VLE calculation similar conversion and product selectivities were achieved.

The VLE at the end of the experiments was also calculated. For this purpose, the quantified amounts of the components after the experiments were used as input values. The calculations were performed with the reaction conditions of 350° C. and 20 bar. Thus, the results approximately represent the system at the end of the reaction (i.e. immediately before cooling the reactor in the autoclave experiment). The result for the mass percentage of $H_2$ and components in the liquid phase is shown in FIG. 6.

Although the amount of alkylphenol decreased as it was consumed in the reaction, the VLE calculation predicted that its distribution between the phases remained roughly constant, with 80% to 87% in the liquid phase. On the other hand, the products, after being formed, should have evaporated to a greater extent than the reactant. Only about 60% of each product should have remained in the liquid phase. Furthermore, propylbenzene should have volatilized to a slightly greater extent than propylcyclohexane.

Materials

The reagents used in HDO experiments were purchased from Sigma-Aldrich and used without further purification, including 2-propylphenol (98%), 3-propylphenol (provided without confirmation of identity or purity) 4-propylphenol (≥97%), tetradecane (≥99%), and ethyl acetate (99.8%). Of the reagents used for analytical calibrations, some were purchased from Sigma-Aldrich, including propylbenzene (98%), propylcyclohexane (99%), 4-propylcyclohexanone (≥99.0%), and 2-isopropylphenol (98%). 4-Propylcyclohexanol (>98.0%, cis- and trans-mixture) was also used as analytical standard and was purchased from Tokyo Chemical Industry. The analytical standards were used without further purification.

The catalyst supports were monoclinic $ZrO_2$, anatase $TiO_2$ and $Nb_2O_5$. The metal precursor was Pt(IV)nitrate solution (15% w/w Pt).

Preparation of Catalysts

The catalysts tested in this phase were 3% $Pt/Nb_2O_5$, 3% $Pt/TiO_2$ and 3% $Pt/ZrO_2$. They were prepared by incipient wetness impregnation. Prior to impregnation, the niobia support had been pressed, ground to 0.25-0.42 mm, and calcined at 500° C. for 7 h. The $TiO_2$ was ground to the same size and calcined at 500° C. for 7 h. The zirconia support was ground to the same size range as the niobia and calcined at 600° C. for 10 h. After impregnation and drying (oven, 100° C.), the Pt catalysts were thermally treated at 350° C. In all cases, calcination proceeded for 3 h at 100 mL/min synthetic air flow.

The catalysts were reduced in $H_2$ atmosphere at 20 bar and 353° C. (or 400° C. when the reaction temperature was 375° C.) for 60 min in the same batch reactor as the HDO experiments, a 100 mL Parr, described below. In all cases, the reactor was stirred at 200 rpm.

HDO Experiments

The reactor used for the experiments was a 100 mL batch by Parr, described below.

After catalyst reduction, the reactor was heated up to reaction temperature. Once the desired temperature was attained, 580 mg reactant, dissolved in 27 ml of tetradecane, was injected into the reaction chamber from the reactor's feed vessel with the aid of hydrogen. The reactor was pressurized with pure hydrogen, and the reaction was allowed to proceed for a given time. Afterwards, the reactor was cooled to room temperature. The reaction time was counted from the moment of injection of the reaction mixture to the start of the cooling. When the reactor was cool, the gas phase was sampled, the reactor was vented, and the product and the catalyst were recovered.

Analysis of Products

The components in the gas phase were identified and quantified by a permanent gas GC analyzer. The components in the organic phases, including the ethyl acetate extracts and filtrates, were identified by GC-MS and quantified by a GC method calibrated with standards. The internal standard was 2-isopropylphenol. The GC instruments were equipped with Zebron ZB-wax Plus columns (60 m×0.25 mm×0.25 µm).

Karl-Fischer titration was performed with some of the organic products in tetradecane.

Calculations and Computer Simulations

In the following sections, the results are presented as conversions, selectivities, and yields. These values were calculated from the concentrations of the reactant and the products obtained from GC analysis. Conversion (X) is defined as:

$$X(\%) = \frac{n_{A,0} - n_{A,f}}{n_{A,0}} \quad (1.1)$$

Where $n_{A,0}$ is the molar amount of reactant at the beginning of the experiment and $n_{A,f}$ is the molar amount of reactant at the end. Selectivity (S) is defined as:

$$S(\%) = \frac{n_P}{n_{A,0} - n_{A,f}} \quad (1.2)$$

Where $n_P$ is the molar amount of product obtained in the experiment.

Vapor-liquid equilibrium (VLE) calculations were performed in Aspen Properties®. Para-tert-butylphenol was used as a surrogate of 4-propylphenol, which is unavailable in Aspen's database. Para-tert-butylphenol had the closest boiling point and molecular mass to 4-propylphenol, compared to all other available phenols. The inputs were either the amounts of $H_2$, tetradecane, 4-propylphenol, propylbenzene, and propylcyclohexane that were fed to the reactor before the experiments or the amounts that were quantified afterwards. The equations of state were solved for a series of temperatures and pressures. Different solution methods were tested and they agreed closely on the results for the alkylphenol and solvent, but they varied widely with respect to $H_2$ solubility in tetradecane. The UNIQUAC method gave the order of magnitude[39] and trend[40] of $H_2$ solubility expected from empirical studies reported in the literature. Aspen provided the mass fraction of the whole vapor phase (Y) and the mass fractions of each component in the vapor phase ($y_i$) and in the liquid phase ($w_i$). The percentages of the mass of each component in the liquid phase were calculated as:

$$m\,\%_{i,l} = \frac{w_i(1-Y)\sum_i m_i}{m_i} \quad (1.3)$$

where $m_i$ is the total mass of component i.

In order to calculate the chemical equilibria of the HDO reactions, the 'Equilibrium Compositions' module of HSC Chemistry software by Outotec Research Oy© was used. The simulations were set up based on the following reactions:

$$C_9H_{12}O + H_2 \rightarrow C_9H_{12} + H_2O \quad (1.4)$$

$$C_9H_{12}O + 4H_2 \rightarrow C_9H_{18} + H_2O \quad (1.5)$$

Two phases were defined, gas and liquid. For each phase, the initial amounts of the components were inputted, $H_2$, 4-propylphenol, propylbenzene, propylcyclohexane, and water. The software allows defining $H_2$ only for the gas phase; hence, the total mass of $H_2$ typically added at the beginning of the experiments at 20 bar was inputted. The amount of 4-propylphenol in each phase was introduced according to the results of the VLE simulations. The initial amounts of all other components were zero. The solvent, tetradecane, was not included, as the software assumes all the species to be reactive.

4-Propylphenol was not available in HSC Chemistry's database. Therefore, the required thermodynamic properties, enthalpy and entropy of formation, as well as the heat capacities at relevant temperatures, were calculated with group contribution methods. The methods by Joback, Benson, and Yoneda were applied as described in Reid et al.'s textbook.[41] The boiling and fusion points and the critical temperature were taken from NIST's online database[42] and Céondo GmbH.[43]

Different non-binding example aspects and embodiments of the present invention have been illustrated in the foregoing. The embodiments are used merely to explain selected aspects or steps that may be utilized when implementing the present invention. Some embodiments may be presented herein only with a reference to a certain aspect of the invention. It should be appreciated that the embodiments may apply to other aspects of the present invention, as well. Consequently, any appropriate combination of the embodiments and the aspects may be formed. Any combination of aspects or embodiments as disclosed herein may also be made without at least one non-essential feature disclosed in an aspect or embodiment.

REFERENCES

(39) Ferrando, N.; Ungerer, P. Hydrogen/Hydrocarbon Phase Equilibrium Modelling with a Cubic Equation of State and a Monte Carlo Method. Fluid Phase Equilib. 2007, 254 (1-2), 211-223.
(40) Hemptinne de, J.-C.; Ledanois, J.-M.; Mougin, P.; Barreau, A. Phase Equilibrium in Presence of $H_2$ or Other Supercritical Gases. In Select Thermodynamic Models for Process Simulation-A Practical Guide Using a Three Steps Methodology; Editions Technip, 2012; p 289.
(41) Reid, R. C.; Prausnitz, J. M.; Poling, B. E. The Properties of Gases and Liquids, 4th Edition; McGraw-Hill: USA, 1987.
(42) U.S. Secretary of Commerce on behalf of the United States of America. Phenol, 4-propyl-https://webbook.nist.gov/cgi/cbook.cgi?ID=C645567&Mask=4 (accessed Jul. 25, 2018).
(43) Céondo GmbH. Chemical Properties of Phenol, 4-propyl-(CAS 645-56-7) https://www.chemeo.com/cid/27-374-7/Phenol % 2C 4-propyl-#ref-joback (accessed Aug. 6, 2018).

The invention claimed is:

1. A process for removing hydroxyl groups from phenolic compounds, the process comprising:
providing in a first reactor at least one hydrodeoxygenation catalyst containing sulphided NiMo, CoMo or NiW;
providing a feedstock containing phenolic compounds;
carrying out hydrodeoxygenation by contacting the feedstock with the hydrodeoxygenation catalyst to obtain a phenolic hydrocarbon feedstock;
providing in a second reactor at least one direct deoxygenation catalyst containing Pt/Nb2O5;
forming a mixture by feeding into the second reactor the phenolic hydrocarbon feedstock and hydrogen gas; and
carrying out direct deoxygenation to the phenolic hydrocarbon feedstock to obtain hydrocarbons in the second reactor with the hydrogen gas included in the formed mixture during the direct deoxygenation, wherein the direct deoxygenation directly cleaves C—O bonds by hydrogenolysis and at least 50 mol-% of the hydroxyl groups originally bonded to phenolic compounds are removed while the aromaticity of the hydrocarbon is preserved.

2. The process of claim 1, wherein the hydrodeoxygenation is carried out at a temperature in a range 270-380° C., at a hydrogen pressure in a range 30-100 bar and WHSV of 2-0.5 1/h.

3. The process of claim 2, wherein the direct deoxygenation is carried out at a temperature in a range of 340-450° C., at a hydrogen pressure in a range of 15-50 bar.

4. The process of claim 3, wherein the phenolic hydrocarbon feedstock contains alkylphenols.

5. The process of claim 4, wherein the phenolic hydrocarbon feedstock is contacted with the catalyst in liquid phase.

6. The process of claim 5, comprising:
obtaining the feedstock from lignocellulosic biomass.

7. The process of claim 6, wherein no water or hydrogen sulfide is added in the first and second reactors during the performance of the process.

8. The process of claim 1, wherein the direct deoxygenation is carried out at a temperature in a range of 340-450° C., at a hydrogen pressure in a range 15-50 bar.

9. The process of claim 1, wherein the phenolic hydrocarbon feedstock contains alkylphenols.

10. The process of claim 9, wherein alkylphenols are converted to alkylbenzenes during direct deoxygenation.

11. The process of claim 1, wherein the phenolic hydrocarbon feedstock is contacted with the catalyst in liquid phase.

12. The process of claim 1, comprising:
obtaining the feedstock from lignocellulosic biomass.

13. The process of claim 1, wherein no water or hydrogen sulfide is added in the first and second reactors during the performance of the process.

14. The process of claim 1, wherein the direct deoxygenation is carried out at a temperature of 350° C., at a hydrogen pressure of 20 bar.

15. The process of claim 1, wherein the direct deoxygenation directly cleaves the C—O bonds by hydrogenolysis without any intermediate hydrogenation steps.

16. The process of claim 1, comprising:
feeding the phenolic hydrocarbon feedstock to the second reactor without chemical modification of the phenolic hydrocarbon feedstock for forming the mixture.

17. A catalytic conversion system, comprising:
a first reactor and a second reactor wherein:
the first reactor is in fluid communication with the second reactor;
wherein the first reactor includes:
at least one catalyst bed comprising sulphided NiMo, CoMo, NiW or a combination thereof;
temperature control system configured to monitor and adjust temperature inside the first reactor;
at least one first inlet for feeding phenolic compounds into the first reactor;
at least one second inlet for feeding hydrogen into the first reactor;

the first reactor configured for hydrodeoxygenation by contacting the phenolic compounds with the hydrodeoxygenation catalyst to produce a phenolic hydrocarbon feedstock;

at least one first outlet for transferring the produced phenolic hydrocarbon feedstock outside the first reactor to the second reactor; and wherein the second reactor includes:

at least one direct deoxygenation catalyst bed containing Pt/Nb2O5 to carry out direct deoxygenation to the phenolic hydrocarbon feedstock received from the first reactor to obtain hydrocarbons while exposed to hydrogen gas in the second reactor during the direct deoxygenation, wherein the direct deoxygenation directly cleaves C—O bonds by hydrogenolysis and at least 50 mol-% of hydroxyl groups originally bonded to the phenolic compounds are removed while aromaticity of the hydrocarbons is preserved;

temperature control system configured to monitor and adjust temperature inside the second reactor;

at least one third inlet for feeding phenolic hydrocarbons into the second reactor;

at least one fourth inlet for feeding the hydrogen gas into the second reactor;

at least one second outlet for transferring a resulting feedstock contains aromatic compounds outside the second reactor; and wherein the second reactor optionally comprises at least one recycle feed line from the at least one second outlet to the at least one third inlet.

18. The system of claim 17, wherein the direct deoxygenation directly cleaves the C—O bonds by hydrogenolysis without any intermediate hydrogenation steps.

19. The system of claim 17, wherein the at least one first outlet for transferring the produced phenolic hydrocarbon feedstock outside the first reactor to the second reactor and the at least one third inlet for feeding phenolic hydrocarbons into the second reactor are configured so that the phenolic hydrocarbon feedstock is feedable to the second reactor without chemical modification of the phenolic hydrocarbon feedstock.

* * * * *